United States Patent [19]
Kretschmann et al.

[11] Patent Number: 5,254,467
[45] Date of Patent: Oct. 19, 1993

[54] FERMENTIVE PRODUCTION OF 1,3-PROPANEDIOL

[75] Inventors: Josef Kretschmann, Langenfeld; Franz-Josef Carduck, Haan; Wolf-Dieter Deckwer, Oldenburg; Carmen Tag, Brunswick; Hanno Biebl, Wolfenbuettel, all of Fed. Rep. of Germany

[73] Assignees: Henkel Kommanditgesellschaft auf Aktien, Duesseldorf; Gesellschaft fuer Biotechnologische Forschung mbH, Brunswick, both of Fed. Rep. of Germany

[21] Appl. No.: 691,648

[22] Filed: Apr. 25, 1991

Related U.S. Application Data

[63] Continuation-in-part of Ser. No. 402,209, Sep. 1, 1989, abandoned.

[30] Foreign Application Priority Data

Sep. 1, 1988 [DE] Fed. Rep. of Germany ....... 3829618
Jul. 24, 1989 [DE] Fed. Rep. of Germany ....... 3924423

[51] Int. Cl.$^5$ ......................... C12P 7/04; C12R 1/145
[52] U.S. Cl. .................................. 435/158; 435/842
[58] Field of Search ............................. 435/158, 842

[56] References Cited

OTHER PUBLICATIONS

Archives of Microbiology (1987), H. Streekstra, pp. 268–275.
Method in Microbiology, 2, Academ, Press s., pp. 277–327.
Averhoff, B., Dürre, P. & Gottschalk, G. (1989). optimization of the anaerobic production of propanediol-1,3 from glycerol by Citrobacter freundii, Poster Annu. Meet. Am. Soc. Microbiol., New Orleans.
Evans, C. G. T., Herbert, D. & Tempest, D. W. (1970), The continuous cultivation of micro-organisms, w. construction of a chemostat, in: Methods in Microbiology, vol. 2, J. P. Norris & D. W. Ribbons (eds), Academic Press, London/New York: 277–327.
Forage, R. G. & Foster, M. A. (1982), Glycerol fermentation in Klebseilla pneumoniae: functions of the coenzyme $B_{12}$–dependent glycerol and diol dehydratases, J. Bacteriol. 149: 413–419.
Forage, R. G. & Lin, E. C. C. (1982), dha system mediating aerobic and anaerobic dissimilation of glycerol in Klebsiella pneumoniae NCIB 418, J. Bacteriol. 151: 591–599.
Forsberg, C. W. (1987), Production of 1,3-propanediol from glycerol by Clostridium a cetobutylicum and other Clostridium species, Appl. Environ. Microbiol. 53: 639–643.
Lin, E. C. C. (1976), Glycerol dissimilation and its regulation in bacteria, Ann, Rev. Microbiol. 30: 535–578.
Mickelson, M. N. & Werkman, C. H. (1940), The dissimilation of glycerol by coli-aerogenes intermediates, J. Bacteriol. 39: 709–715.
Mickelson, M. N. & Werkman, C. H. (1940), Formation of trimethyleneglycol from glycerol by Aerobacter, Enzymologia 8: 252–256.
Nakas, J. P., Schaedle, M., Parkinson, C. M., Coonley, C. E. & Tanenbaum, S. W. (1983a), System development for linked-fermentation production of solvents from algal biomass, appl. Environ. Microbiol. 46: 1017–1023.
Nanninga, H. J. & Gottschal, J. C. (1987), Properties of Desulfovibrio carbinolicus sp. nov. and other sul- (List continued on next page.)

Primary Examiner—Herbert J. Lilling
Attorney, Agent, or Firm—Ernest G. Szoke; Wayne C. Jaeschke; John E. Drach

[57] ABSTRACT

A process for the transformation of glycerol into 1,3-propanediol by microorganisms comprising fermenting the microorganisms in media having a glycerol content of from about 5% to about 20% by weight under standard anaerobic fermentation conditions and recovering the 1,3-propanediol. The microorganisms according to the invention do not suffer catabolic repression by the large amount of 1,3-propanediol produced by the process.

16 Claims, No Drawings

OTHER PUBLICATIONS fate-reducing bacteria isolated from an anaerobic α purification plant, Appl. Environ. Microbiol. 53: 802-809.

Neijssel, O. M., Hueting S., Crabbendam, K. J. & Tempest D. W. (1975), Dual pathways of glycerol assimilation in Klebsiella aerogenes NCIB 418. Their regulation and possible functional significance, Arch. Microbiol. 104: 83-87.

Ruch, F. E., Lengeler, J. & Lin, E. C. C. (1974), Regulation of glycerol catabolism in Klebsiella aerogenes, J. Bacteriol. 119: 50-56.

Ruch, F. E. & Lin, E. C. C. (1975), Independent constitutive expression of the aerobic and anaerobic pathways of glycerol catabolism in Klebsiella aerogenes, J. Bacteriol. 124: 348-352.

Schink, B. & Stieb, M. (1983), Fermentative degradation of polyethylene glycol by a strictly anaerobic gram-negative nonsporeforming bacterium, Pelobacter venetianus sp. Nov., Appl. Environ. Microbiol. 45: 1905-1913.

Schutz, H. & Radler, F. (1984), Anaerobic reduction of glycerol to propanediol-1,3 by Lactobacillus brevis and Lactobacillus buchneri, System. Appl. Microbiol. 5: 169-178.

Slininger, P. J., Bothast, R. J. & Smilety, K. L. (1983), Production of 3-hydrosypropionaldehyde from glycerol, Appl. Environ. Microbiol. 46: 62-67.

Sobolov, M. & Smilety, K. L. (1960), Metabolism of glycerol by an acrolein-forming Lactobacillus, J. Bacteriol. 79: 261 ∝ 266.

Stieb, M. & Schink, B. (1984), A new e-hydroxybutyrate fermenting anaerobe, Ilyobacter polytropus, gen. nov. sp. nov., possessing various fermentation pathways, Arch. Microbiol. 140: 139-146.

Streekstra, H., Teixeira de Mattos, M. J., Neijssel, O. M. & Tempest, D. W. (1987), Overflow metabolism during anaerobic growth of Klebsiella aerogenes NCTC 418 on glycerol and dihydroxyacetone in chemostat culture, Arch. Microbiol. 147: 268-275.

Toraya, T., Kuno. S. & Fukui, S. (1980), Distribution of coenzyme $B_{12}$-dependent diol dehydratase and glycerol dehydratase in selected genera of Enterobacterlaceae and Propionibacteriaceae, J. Bacteriol. 141: 1439-1442.

Tran-Dinh, K. & Hill, F. (1986), The role of cobalt in the fermentation of glycerol to 1,3-propanediol and 2,3-butanediol by Klebsiella pneumoniae, Poster Gemeinsame Frühjahrstagung der VAAM und der Sektion I der DGHM, Münster.

Tran-Dinh, K. & Hill, F. F. (1989), Verfahren zur Herstellung von Propandiol-(1,3), in: Offenlegungsschrift des Deutschen Patentamtes, Patent DE 3734764 A1.

Voisenet, E. (1914), Sur un ferment contenu dans lex eaus agent de déshydratation de la glycérine, Ann. Inst. Pasteur 28: 807-818.

Voisenet, E. (1918), Sur une bactérie de l'eau végetant dans les vins amers capable de déshydrater la glycérine glycéroréaction, Ann. Inst. Pasteur 32: 576-510.

FERMENTIVE PRODUCTION OF 1,3-PROPANEDIOL

CROSS-REFERENCE TO RELATED APPLICATIONS

This is a continuation-in-part of application Ser. No. 07/402,209 filed on 09/01/89, now abandoned.

BACKGROUND OF THE INVENTION

1. Field of the Invention

This invention relates to a process for the transformation of glycerol into 1,3-propanediol on an industrial scale by means of preferably anaerobic microorganisms.

2. Description of the Related Art

In the oleochemical transformation of fatty acid triglycerides into fatty acid derivatives, such as fatty acid methyl esters or fatty alcohols, glycerol is formed from the splitting of the triglycerides.

It is known from the scientific literature that a number of microorganisms, including above all anaerobic microorganisms, are capable of growing on glycerol and of transforming glycerol in the process into other products. One of the metabolites observed in this process is 1,3-propanediol.

1,3-Propanediol is a diol with many applications which, in principle, may be used for the same purposes as ethylene glycol, propylene glycol (1,2-propanediol) or butanediol. Hitherto, 1,3-propanediol has been obtained by addition of water onto acrolein and subsequent hydrogenation. However, the chemical process is so expensive that the end products obtained are unsuitable for many potential applications on account of their high price.

The transformation of glycerol into 1,3-propanediol by microorganisms is mentioned in a few places in the scientific literature. Thus, the metabolism of glycerol by *Klebsiella aerogenes* NCTC 418 in chemostat cultures is described by H. Streekstra et al in Arch. Microbiol. (1987), 147: 268-275. Although the action of a special Klebsiella aerogenes strain on glycerol in different media is discussed in this Article, there is nothing to help the expert to evaluate the special metabolic performances of such organisms for an industrial process. Applied and Environmental Microbiology, April 1987, pages 639–643, teaches that Clostridium butyricum NRRL B593 and Clostridium butyricum NRCC 33007 grow with glycerol in batch and Chemostat culture conditions. The same paper also teaches that Clostridium butyricum NRRL B593 and Clostridium butyricum NRCC 33007 grow in a chemically defined medium containing 2% (wt/vol) glycerol as the sole carbon source producing 1,3-propanediol as the major fermentation product. The reference does not teach or suggest that any microorganism disclosed therein will not be catabolically repressed by elevated 1,3-propanediol concentrations.

The problem addressed by the present invention is to provide an industrially workable process for the transformation of glycerol into i,3-propanediol in media having a glycerol content of from about 5% to about 20% by weight by microorganisms which do not suffer catabolic repression by the correspondingly high 1,3-propanediol produced by the process. Additionally, this process is intended to use triglyceride processing streams accumulating in the industrial processing of triglycerides as its starting material.

More particularly, the problem addressed by the invention is to provide a corresponding process which starts out from strains of which the fermentation is easy to handle on an industrial scale and which are capable of converting high concentrations of glycerol into propanediol under standard fermentation conditions with a volume/time yield of more than 0.5 g $h^{-1}\cdot l^{-1}$ without the expected catabolic repression which is normally encountered with media accumulating such high 1,3-propanediol concentrations. The strains which can be used in the process include Clostridium butyricum SH 1 (DSM 5431) and AK 1 (DSM 5430) and also from Klebsiella pneumoniae strains, such as K. pneumoniae DSM 2026, and also K. oxytoca NRCC 3006.

SUMMARY OF THE INVENTION

The present invention provides a process for the transformation of glycerol into 1,3-propanediol in a medium which contains from about 5% to about 20% by weight of glycerol which comprises fermenting under standard anaerobic fermentation conditions and constant pH a microorganism strain selected from the group consisting of Clostridium butyricum SH (DSM 5431), Clostridium butyricum AK 1 (DSM 5430), Klebsiella pneumoniae DSM 2026, Klebsiella oxytoca NRCC 3006 and mutants thereof in a nutrient medium comprised of an aqueous glycerol solution having glycerol to produce a biomass and 1,3-propanediol solution in a volume/time yield of more than 0.5 $g\cdot h^{-1}\cdot l^{-1}$ and separating the 1,3-propanediol solution from the biomass. The microorganisms according to the invention do not suffer catabolic repression by the large amount of 1,3-propanediol produced by the process.

In a broad embodiment, the invention starts out from the basic concept that many anaerobic microorganisms and some aerobic microorganisms have an enzyme supply which enables glycerol to be transformed into 1,3-propanediol. According to the invention, therefore, potentially suitable strains are selected on the basis of their efficiency in a first step. To this end, strains from the groups clostridium, enterobacterium, lactobacillus, bacillus, citrobacter, aerobacter and/or klebsiella are selected and allowed to grow under standard fermentation conditions on a 5% glycerol solution as sole carbon source, the volume/time yield is determined and those strains which produce a volume/time yield over the limit mentioned are selected. In the present context, under standard fermentation conditions means that, after culture in a standard medium, as recommended for example by the strain collections, the microorganism is transferred to a salt medium which also contains an N source, for example yeast extract, but only glycerol as the carbon and energy source. A suitable standard medium for klebsiella in particular can be found in Example 2 (fermenter medium). It may be adapted for other strains in accordance with literature data.

According the invention, the pH value has to be kept constant or regulated under industrial fermentation conditions. Suitable pH values are in the range from 6 to 9 and more especially in the range from 6.5 to 8.

According to the invention, it has been found that particularly suitable strains may be selected from one of the following groups of microorganisms: *Clostridium perfringens, Clostridium pasteurianum, Clostridium acetobutylicum, Clostridium butylicum, Clostridium butyricum, Clostridium beijerinckii, Clostridium kantontoi,*

*Lactobacillus brevis, Lactobacillus buchneri, Citrobacter freundii, Aerobacter aerogenes, Klebsiella pneumoniae, Citrobacter intermedium, Klebsiella aerogenes* or *Klebsiella oxytoca*. Of these, *Clostridium butyricum* SH 1 (DSM 5431), *Clostridium butyricum* AK 1 (DSM 5430), *Klebsiella pneumoniae* DSM 2026, Klebsiella oxytoca NRCC 3006 and mutants thereof are particularly preferred. Other suitable strains are *Klebsiella planticola*, particularly *Klebsiella planticola* IAM 1133 and mutants and variants thereof. It is clear to the expert that the enzyme supply of the strains is the key criterion. Accordingly, the invention also encompasses strains to which the enzyme supply important for the conversion of glycerol to 1,3-propanediol has been transferred by genetic engineering methods.

Particularly preferred strains for carrying out the process according to the invention are the strains *Clostridium butyricum* SH 1 (DSM 5431) and AK 1 (DSM 5430). These strains were enriched for propanediol formation from earth and mud samples in glycerol-containing media after the samples had been pasteurized. The strains exhibit the following properties: growth in PY medium without carbohydrate, growth in glucose mineral salt biotin medium, no hydrolysis of gelatine, the sugar utilization spectrum corresponds to *Clostridium acetobutyricum* in regard to utilization of the sugars melecistose and ribose. The strains mentioned are so preferred to the Klebsiella strains that they may be placed in risk class 1 (as against 2). They show particularly high glycerol conversion in the process according to the invention.

According to the invention, it has been found that unusually high glycerol concentrations—differing from the microbiological norm—of up to 20% by weight, preferably from 5 to 15% by weight and more preferably from 10 to 15% by weight may be used. This is all the more surprising insofar as catabolite repression of the growth of the microorganisms according to the invention would normally have been expected to occur by the correspondingly large amounts of 1,3-propanediol produced by the process according to the invention. Some Clostridium strains did not grow at all in glycerol media. These strains include Clostridium butyricum NRRL B593 and *Clostridium butyricum* NRCC 33007. However, the strains according to the invention were found to grow in high glycerol concentrations. For example, *Clostridium butyricum* SH 1 (DSM5431) is able to grow in a medium containing about 8.8% by weight glycerol with about 94% consumption and produce 42 grams/liter of 1,3-propanediol at a rate of 1.9 grams/liter/hour. *Clostridium butyricum* AK 1 (DSM 5430) is able to grow in a medium containing about 11.1% by weight glycerol with about 94% consumption and produce 58 grams/liter of 1,3-propanediol at a rate of 2.3 grams/liter/hour. Growth under the above conditions is unexpected in light of the catabolic repression which is normally encountered with media accumulating such high 1,3-propanediol concentrations.

The process according to the invention may be carried out not only with solutions of pure glycerol, but generally with triglyceride processing streams which are aqueous glycerol solutions from the industrial processing of triglycerides, for example from the hydrogenation of fatty acid triglycerides with steam or from the transesterification of fatty acid triglycerides. Triglyceride processing streams such as these mainly contain water and glycerol although a few impurities emanating from the starting materials or from the process are also present.

According to the invention, it has been found that untreated triglyceride processing streams are preferred starting materials, those from the hydrogenation of tallow and other triglycerides low in lauric acid being particularly preferred starting materials. Triglycerides low in lauric acid are those which contain equal to or less than about 20% by weight lauric acid.

To carry out the process according to the invention, the microorganism strains selected in accordance with the invention are preferably first cultured in a preculture medium. Suitable preculture media are salt media additionally containing glycerol and/or other carbon sources, such as glucose for example, and nitrogen sources, such as yeast extract for example.

The preculture step is preferably continued until enough biomass for charging the fermenter has formed. The fermenter is generally charged when the carbon source of the preculture has been used up completely or substantially completely.

The fermenter media differ from the preculture media in the fact that they contain comparatively smaller quantities of phosphate and of potassium.

Generally, both the preculture and the fermenter media may contain the cations sodium, potassium, ammonium, magnesium and calcium and the anions phosphate, sulfate, chloride.

In addition, the fermenter media preferably also contain trace amounts of the elements particularly zinc, iron, manganese, copper, cobalt, boron and/or molybdenum. A trace amount is understood to be equal to from about 0.01mg/l to about 50mg/l.

The exact composition of the fermentation media can be found by the expert in the relevant specialist literature or even in the recommendations of the strain collections. Information can be found, for example, in C. G. T. Evans, D. Hebert & D. W. Tempest, 1970 "The Continuous Cultivation of Micro-organisms, 2. Construction of a Chemostat", Methods in Microbiology, 2, Academic Press, pages 277–327 and in H. Streekstra, M. J. Teixeira de Mattos, O. M. Neijssel & D. W. Tempest, 1987 "Overflow Metabolism during Anaerobic Growth of Klebsiella aerogenes NTCC 418 on Glycerol and Dihydroxyacetone in Chemostat Culture", Archives of Microbiology, 147, pages 268–275.

Where anaerobic strains are used, fermentation is carried out in the absence of oxygen, preferably in a nitrogen atmosphere. In one preferred embodiment, fermentation is carried out in the atmosphere of the gaseous secondary fermentation products.

To carry out the process on an industrial scale, a suitable inoculum may be introduced into preculture vessels and then combined with the nutrient solution. The quantity of inoculum, based on the batch as a whole, is preferably from 5 to 20% by volume and more preferably from 8 to 15% by volume. The resulting suspension of microorganisms in the solution is then charged with glycerol in a fermentation tank or in a cascade of fermentation tanks. Other auxiliaries may then be added in this fermenter or in another fermenter of the cascade. For example, foam inhibitors or even filtration aids may be added. For harvesting, the culture broth is then either separated from the biomass in a membrane filter press in a batch operation or the valuable product is continuously separated off by a filtration process, for example by microfiltration. After the biomass formed has been washed out and the washing water combined with the filtrate, water and low-boiling constituents may be continuously or discontinuously removed at least partly in another step carried out in an evaporator. The relatively high-boiling constituents leaving the evaporator, i.e. mixtures of the nutrient salts with fermentation products, may then be introduced, for example, into a thin-layer evaporator. The resulting condensate may be separated by rectification and short-path distillation, after which 1,3-propanediol and, if desired, such secondary products as 2,3-butanediol are obtained.

The process according to the invention enables glycerol to be converted substantially stoichiometrically into 1,3-propanediol. The yield of 1,3-propanediol is often of the order of 2 mol 1,3-propanediol from 3 mol glycerol. In the present context, substantially is understood to mean a glycerol consumption of at least 80%, preferably 95% and, in particular, more than 99%.

|  | Glucose | 3.00 g/l |
|---|---|---|

The medium is adjusted to pH 2 before autoclaving.

Cultivation

The organism was cultured on the salt medium overnight. The culture was incubated under anaerobic conditions ($N_2$ gas phase) at 37° C. in 100 ml culture bottles. After incubation, quantities of 1 ml culture broth were used as inoculum for the growth tests. Two parallel tests were carried out in each case using three different glycerol sources. The medium used was the above-mentioned salt medium in which the glucose was replaced by quantities of 20 g/l glycerol, glycerol from the hydrogenation of beef tallow with steam and glycerol from the hydrogenation of coconut oil with superheated steam.

TABLE I

Use of glycerols of different origin for the microbial production of 1,3-propanediol (bottle tests with *Klebsiella pneumoniae* (DSM 2026))

| Feed | Max. increase in Opt. | Glycerol starting Concentration (mM) | Glycerol consumption (%) | Glycerol consumption (mM) | Ethanol $(mM)^2$ | Ethanol $(\%)^1$ | Acetate $(mM)^2$ | Acetate $(\%)^1$ | Acetoin $(mM)^2$ | Acetoin $(\%)^1$ | 2,3-butanediol $(mM)^2$ | 2,3-butanediol $(\%)^1$ | 1,3-propanediol $(mM)^2$ | 1,3-propanediol $(\%)^1$ |
|---|---|---|---|---|---|---|---|---|---|---|---|---|---|---|
| Glycerol | 1.18 | 212.5 | 50.8 | 108.2 | 2.9 | 2.8 | 18.0 | 16.9 | 0.3 | 0.2 | 12.5 | 11.7 | 81.4 | 76.4 |
| Tallow glycerol | 1.26 | 198.4 | 52.6 | 104.4 | 3.6 | 3.5 | 19.6 | 18.8 | 2.4 | 2.3 | 8.8 | 8.5 | 82.4 | 79.1 |
| Coconut oil | 1.15 | 208.2 | 54.6 | 114.2 | 3.8 | 3.3 | 19.5 | 17.4 | 1.8 | 1.6 | 7.3 | 6.4 | 70.1 | 61.9 |

[1] mmol product/100 mmol metabo. glycerol
[2] concentrations after incubation for 48 h Other important valuable products, including for example 2,3-butanediol, ethanol or acetoin, 2,3-butanediol, ethanol or acetic acid and/or lactic acid, may be formed in addition to 1,3-propanediol.

It has been found that fermentation is best carried out in a fermenter equipped with a laminar-flow stirrer of low shear rate. Stirrers of this type are well known to the expert in the field in question. The laminar flow avoids high shear rates which could have an adverse effect in the present case.

In addition, it preferred to keep the power input small. The expert will adjust the power input in such a way that, for a fermentation temperature in the range from 27° to 40° C. and preferably in the range from 33° to 38° C., the power input is sufficient to maintain the fermentation temperature without increasing it. Thus, the power input is preferably less than 1 KWh/m$^3$ and more preferably between 0.75 and 0.2 KWh/m$^3$.

The following examples are meant to illustrate but not to limit the invention.

EXAMPLES

Example 1

Bottle tests on the growth of *Klebsiella pneumoniae* on various glycerol sources Organism: *Klebsiella pneumoniae* DSM 2026.

| Medium: | |
|---|---|
| $K_2HPO_4$ | 3.383 g/l |
| $KH_2PO_4$ | 1.293 g/l |
| $NH_4Cl$ | 5.35 g/l |
| $Na_2SO_4.10H_2O$ | 0.64 g/l |
| Citric acid.$H_2O$ | 0.42 g/l |
| $MgCl_2$ | 0.12 g/l |
| $CaCl_2$ | 0.0022 g/l |
| Yeast extract | 1.00 g/l |

Example 2

Batch fermentation of glycerol to 1,3-propanediol
Organism: *Klebsiella pneumoniae* DSM 2026

| Medium: Preculture medium: | |
|---|---|
| $K_2HPO_4$ | 3.383 g/l |
| $KH_2PO_4$ | 1.293 g/l |
| $NH_4Cl$ | 5.35 g/l |
| $Na_2SO_4.10H_2O$ | 0.64 g/l |
| Citric acid.$H_2O$ | 0.42 g/l |
| $MgCl_2$ | 0.12 g/l |
| $CaCl_2$ | 0.0022 g/l |
| Glycerol | 20.00 g/l |
| Yeast extract | 1.00 g/l |
| Glucose | 3.00 g/l |

The medium was adjusted to pH 7.2 before autoclaving.

| Fermenter medium | |
|---|---|
| $NaH_2PO_4.2H_2O$ | 1.56 g/l |
| $NH_4Cl$ | 5.35 g/l |
| KCl | 0.75 g/l |
| $Na_2SO_4.10H_2O$ | 0.64 g/l |
| Citric acid.$H_2O$ | 0.42 g/l |
| $MgCl_2$ | 0.12 g/l |
| $CaCl_2$ | 0.0022 g/l |
| Glycerol | as shown in the Table |
| Yeast extract | 1.00 g/l |

Trace element concentration

Both media contained the following concentrations of trace elements:

| | |
|---|---|
| ZnCl$_2$ | 3.42 mg/l |
| FeCl$_3$.6H$_2$O | 27.00 mg/l |
| MnCl$_2$.4H$_2$O | 10.00 mg/l |
| CuCl$_2$.2H$_2$O | 0.88 mg/l |
| CoCl$_2$.6H$_2$O | 2.38 mg/l |
| H$_3$BO$_3$ | 0.31 mg/l |
| Na$_2$MoO$_4$ | 0.02 mg/l |

Foam inhibitors

Additions of a commercially available foam inhibitor were made during the fermentations.

Cultivation

The inoculum (5%) was prepared by cultivation under anaerobic conditions (N$_2$ gas phase) for about 24 hours at 37° C. in culture bottles.

The fermentations were carried out in a 4.5 liter fermenter of the type manufactured by SGI (Setric Genie Industriel) with an SGI temp., pH and r.p.m. measuring and control system. The fermentations were carried out under anaerobic conditions (N$_2$ gas phase) at 37° C./pH 7 (regulated by addition of 2.5 N NaOH) on a simple salt medium (0.1% yeast extract) containing 50, 100, 150 and 200 g/l glycerol (p.A.).

The results of the fermentations are shown in the following Table.

In the fermentations with 50 and 100 g/l glycerol, 99% of the substrate was converted. In the tests with 150 g/l, approx. 90% of the glycerol was converted.

The highest 1,3-propanediol concentration was achieved at 150 g/l: 759 mM or 58 g/l; the highest volume/time yield (VTY) was achieved at a glycerol concentration of 100 g/l: 2.3 g·h$^{-1}$·l$^{-1}$.

Similar batch fermentations were carried out with strains of Citrobacter freundii on a 1 l scale. The strain Cirobacter freundii DSM 30039, which appears particularly successful, showed a favorable product scheme in fermentations with 50 g/l glycerol.

TABLE II

| | Microbial conversion of glycerol to 1,3-propanediol at various starting concentrations of glycerol | | | | | | | |
|---|---|---|---|---|---|---|---|---|
| Strain | Glycerol concentration (g/l) | Glycerol consumption (mol-%) | Ethanol (mM) | Ethanol (mol-%) | Acetate (mM) | Acetate (mol-%) | 2,3-butanediol (mM) | 2,3-butanediol (mol-%) |
| K. pneumoniae DSM 2026 | 50.9 | 99.4 | 22.8 | 4.1 | 87.6 | 15.9 | 3.6 | 0.7 |
| | 96.9 | 99.9 | 65.0 | 6.2 | 188.2 | 17.9 | 10.4 | 1.0 |
| | 154.1 | 88.5 | 110.5 | 7.5 | 205.5 | 13.9 | 10.8 | 0.7 |
| | 201.7 | 53.0 | 91.5 | 7.9 | 108.5 | 9.3 | 1.4 | 0.1 |
| Citrobactor freundii | 52.9 | 100.0 | 10.7 | 1.8 | 134.1 | 23.1 | — | — |

| Strain | D(−)lactate (mM) | D(−)lactate (mol-%) | 1,3-propanediol (mM) | 1,3-propanediol (mol-%) | 1,3-propanediol (g/l) | VTY (g·h$^{-1}$·l$^{-1}$) | Yield based on theor. max. (66.66%) |
|---|---|---|---|---|---|---|---|
| K. pneumoniae | 32.3 | 5.9 | 294.4 | 53.5 | 22.4 | 1.4 | 80 |
| | 39.7 | 3.8 | 568.4 | 54.0 | 43.2 | 2.3 | 81 |
| | 169.6 | 11.4 | 759.2 | 51.2 | 57.7 | 1.5 | 77 |
| | 122.7 | 10.6 | 419.5 | 36.1 | 31.9 | 0.4 | 54 |
| Citrobacter freundii | 12.7 | 2.1 | 370.0 | 64.0 | 28.2 | 1.2 | 96 |

Example 3

Further fermentations were carried out under the same conditions as in Example 2. Fermentation was carried out at 37° C., 200 min$^{-1}$ and pH 7 (regulated by addition of 5 N NaOH) with a working volume of 3 l. During the tests, the reactors were purged with nitrogen to maintain anaerobic conditions (0.3 NL/min.).

Crude glycerol from beef tallow was used in two different fermentations in which the glycerol concentration was varied (90 and 140 g/l). In both tests, more than 90% of the glycerol available was metabolized. The results obtained are shown in the following Table:

TABLE III

| | Results of batch fermentations on beef tallow | | | | | | | | | |
|---|---|---|---|---|---|---|---|---|---|---|
| Glycerol source | Glycerol concentration (g/l) | Glycerol consumption (mol-%) | Ethanol (mM) | Acetate (mM) | 2,3-butanediol (mM) | D(−)lactate (mM) | 1,3-propanediol (mM) | 1,3-propanediol (g/l) | VTY (g·h$^{-1}$·l$^{-1}$) | 1,3-propanediol yield, based on theor. max. (66.66%) |
| Beef tallow (Henkel) | 89.9 | 99.9 | 69.7 | 168.8 | 15.4 | 43.7 | 548.5 | 41.7 | 2.0 | 84 |
| | 139.3 | 99.1 | 174.4 | 186.0 | 11.2 | 184.7 | 807.5 | 61.4 | 1.7 | 81 |

Example 4

The tests were repeated with the strains Clostridium butyricum SH 1 and AK 1 as batch cultures, culture volume approx. 700 ml, in a 1-liter fermenter (BCC). The medium had the following composition (quantities per liter): K$_2$HPO$_4$ 1 g, KH$_2$PO$_4$ 0.5 g, (NH$_4$)$_2$SO$_4$ 5 g/100 g glycerol, MgSO$_4$ 7H$_2$O 0.2 g, CaCl$_2$·2H$_2$O 20 mg, FeSO$_4$·7H$_2$O 5 mg, yeast extract 1 g, trace element solution, glycerol as shown. The pH value was kept constant at pH 7 in every case and the temperature was 32° C. FED batch cultures were similarly carried out with glycerol after feeding. The results are shown in Tables 4, 5, 6 and 7.

TABLE 4

Fermentation of glycerol by Clostridium SH 1 and AK 1

| Strain | Glycerol Available % | Glycerol Available mmol/l | Glycerol Consumed mmol/l | O.D. 660 nm | $\mu_{max}$ h$^{-1}$ | Product (mmol/l) 1,3-propanediol | Product (mmol/l) Acetic acid | Product (mmol/l) Butyric acid | Glycerol for product (%) Total | Glycerol for product (%) Diol |
|---|---|---|---|---|---|---|---|---|---|---|
| SH 1 | 2 | 240 | 240 | 3.4 | 0.56 | 153 | 26 | 18 | 90 | 64 |
| | 5 | 554 | 554 | 6.2 | 0.42 | 381 | 31 | 46 | 91 | 68 |
| | 11 | 1197 | 1087 | 6.2 | 0.27 | 740 | 18 | 128 | 93 | 68 |
| | Fb* | 956 | 896 | 5.2 | — | 550 | 41 | 83 | 85 | 61 |
| AK 1 | 2 | 236 | 229 | 2.9 | 0.56 | 143 | 9 | 26 | 82 | 62 |
| | 5 | 516 | 516 | 4.4 | 0.30 | 388 | 46 | 46 | (102) | (75) |
| | FB* | 1203 | 1137 | 5.3 | — | 774 | 85 | 96 | 92 | 68 |

*Fed-batch culture

TABLE 5

Fermentation of glycerol by clostridium SH 1 and AK

| Strain | Glycerol % | Consumed g/l | Time h | Products (g/l) 1,3-propanediol | Products (g/l) Acetic acid + Butyric acid | Productivity g/l·h Glycerol | Productivity g/l·h Diol |
|---|---|---|---|---|---|---|---|
| SH 1 | 2 | 22.1 | 9.5 | 11.6 | 2.2 | 2.3 | 1.2 |
| | 5 | 51.0 | 13 | 30.0 | 5.8 | 3.9 | 2.2 |
| | 11 | 100.0 | 29 | 56.2 | 11.2 | 3.4 | 1.9 |
| | FB* | 82.4 | 22 | 41.8 | 9.4 | 3.7 | 1.9 |
| AK 1 | 2 | 21.1 | 9.5 | 10.7 | 2.8 | 2.2 | 1.4 |
| | 5 | 47.5 | 14.5 | 29.5 | 6.8 | 3.3 | 2.0 |
| | FB* | 104.6 | 26 | 58.8 | 13.5 | 4.0 | 2.3 |

*Fed-batch culture

TABLE 6

Fermentation of crude glycerol by Clostridium SH

| No. | Glycerol content % | Glycerol batch | Lag-phase h | Maximum KOH-consumption rate* mmol/l·h |
|---|---|---|---|---|
| 1 | 2 | crude, from beef tallow | 2 | 24 |
| 2 | 2 | crude, from coconut oil | 9 | 16 |
| 3 | 5 | crude, from beef tallow | 4 | 24 |
| 4 | 5 | from beef tallow, inoculated with 2 | 2 | 30 |
| 5 | 5 | crude, from coconut oil | 9 | 14 |
| 6 | 5 | from coconut oil, inoculated with 3 | 8 | 8 |

*The KOH consumption rate is equivalent to the glycerol consumption rate

TABLE 7

Conversion of 2% glycerol by Clostridium SH 1 as a function of pH

| pH value | Fermentation time h | Glycerol converted g/l | Products as glycerol Propanediol % | Products as glycerol acetic acid % | Products as glycerol butyric acid % |
|---|---|---|---|---|---|
| 5 | (7) | 6 | 62 | 3 | 34 |
| 6 | 12 | 20 | 67 | 7 | 25 |
| 7 | 8 | 20 | 76 | 7 | 17 |
| 7.5 | 12 | 20 | 73 | 12 | 14 |

What is claimed is:

1. A process for the transformation of glycerol into 1,3-propanediol by microorganisms comprising the steps of: (a) fermenting under standard anaerobic fermentation conditions and constant pH a microorganism strain selected from the group consisting of *Clostridium butyricum* SH 1 (DSM 5431) and *Clostridium butyricum* AK 1 (DSM 5430) and mutants thereof in a nutrient medium comprised of an aqueous glycerol solution having from about 5% to about 20% by weight glycerol to produce a biomass and 1,3-propanediol solution in a volume/time yield of more than 2.2g·h$^{-1}$·a$^{-1}$, and (b) separating said 1,3-propanediol solution from said biomass.

2. The process of claim 1 wherein said glycerol solution is a triglyceride processing stream.

3. The process of claim 2 wherein said triglyceride processing stream is an untreated stream from the saponification or transesterification of fats.

4. The process of claim 3 wherein said triglyceride processing stream is a stream from the saponification of fats having a low lauric acid content.

5. The process of claim 1 wherein said aqueous glycerol solution contains from about 10% to about 15% by weight glycerol.

6. The process of claim 1 wherein said pH is maintained at a value of from about 6.5 to about 8.

7. The process of claim 1 wherein the quantity of inoculum for fermentation is from about 5% to about 20% by volume.

8. The process of claim 1 wherein said microorganism strain is Clostridium butyricum SH 1 (DSM 5431) and mutants thereof.

9. The process of claim 1 wherein said microorganism strain is Clostridium butyricum AK 1 (DSM 5430) and mutants thereof.

10. The process of claim 1 wherein said nutrient medium further comprises a salt fermentation medium containing yeast extract as nitrogen source.

11. The process of claim 1 wherein said nutrient medium further comprises trace amounts of elements selected from the group consisting of zinc, iron, manganese, copper, cobalt, boron, molybdenum or combinations thereof.

12. The process of claim 1 wherein the fermentation is carried out a temperature of from about 27° C. to about 40° C.

13. The process of claim 1 wherein said separating step is accomplished by means of a membrane filter press in a batch process or by microfiltration in a continuous process.

14. The process of claim 1 further comprising the step of (c) separating said 1,3-propanediol from said 1,3-propanediol solution.

15. The process of claim 1 wherein said process is carried out in a fermenter having a laminar-flow stirrer.

16. The process of claim 15 wherein the power input to said stirrer is less than 1.0 KWh/m$^3$·h.

* * * * *